(12) United States Patent
Agarwal et al.

(10) Patent No.: US 11,497,293 B2
(45) Date of Patent: Nov. 15, 2022

(54) SYSTEM FOR APPLYING AT LEAST TWO KINDS OF LIQUID ONTO RESPECTIVE TARGETED AREAS OF A SUBSTRATE AND METHOD THEREFOR

(71) Applicant: L'Oreal, Paris (FR)

(72) Inventors: Gaurav Agarwal, Kawasaki (JP); Hiroyuki Ogata, Kawasaki (JP)

(73) Assignee: L'Oreal, Paris (FR)

( * ) Notice: Subject to any disclaimer, the term of this patent is extended or adjusted under 35 U.S.C. 154(b) by 239 days.

(21) Appl. No.: 16/489,621

(22) PCT Filed: Jan. 31, 2018

(86) PCT No.: PCT/JP2018/004102
§ 371 (c)(1),
(2) Date: Aug. 28, 2019

(87) PCT Pub. No.: WO2018/179869
PCT Pub. Date: Oct. 4, 2018

(65) Prior Publication Data
US 2020/0015573 A1    Jan. 16, 2020

(30) Foreign Application Priority Data
Mar. 31, 2017    (JP) .............................. JP2017-070549

(51) Int. Cl.
*A45D 44/00*        (2006.01)
*B41J 3/407*        (2006.01)
(Continued)

(52) U.S. Cl.
CPC ............ *A45D 44/002* (2013.01); *B05B 12/04* (2013.01); *B41J 3/407* (2013.01);
(Continued)

(58) Field of Classification Search
None
See application file for complete search history.

(56) References Cited

U.S. PATENT DOCUMENTS 7,067,170 B2 *    6/2006    Marcus ............... H01L 51/0002
                                                427/255.6
7,431,439 B2 *    10/2008    Fujioka ................ B41J 2/17596
                                                347/85
(Continued)

FOREIGN PATENT DOCUMENTS

CN        101933890 A        1/2011
CN        105030553 A        11/2015
(Continued)

OTHER PUBLICATIONS

Machine Generated English Translation of the abstract of CN101933890. Published Jan. 5, 2011. (Year: 2011).*
(Continued)

*Primary Examiner* — Sylvia Macarthur
(74) *Attorney, Agent, or Firm* — Christensen O'Connor Johnson Kindness PLLC (57) ABSTRACT

The present invention relates to a system (1) for applying at least two kinds of liquid onto respective targeted areas of a substrate (S). The system (1) includes first and second storage unit (10a, 10b) that accommodate first and second liquids ($F_1$, $F_2$); a pressured gas supply unit (20) that is fluidly connected to the first and second storage unit (10a, 10b); first and second applicator (30a, 30b) that are fluidly connected to the first and second storage unit (10a, 10b); and a controller (40) that is operatively connected to the applicator (30a, 30b). The pressured gas supply unit (20) causes pressure of a pressured gas to act on the liquids ($F_1$, $F_2$) within the storage unit (10a, 10b). The first and second applicator (30a, 30b) each include at least one nozzle (300a, 300b) disposed so as to face the substrate (S). The first and
(Continued)

second applicator (30a, 30b) spray the first and second liquids ($F_1$, $F_2$) within the first and second storage unit (10a, 10b) from the nozzles (300a, 300b) toward the substrate (S) by the action of the pressured gas from the pressured gas supply unit (20). The controller (40) individually controls the first and second applicator (30a, 30b) so that the first applicator (30a) sprays the first liquid ($F_1$) toward a targeted area for the first liquid ($F_1$) on the substrate (S) and the second applicator (30b) sprays the second liquid ($F_2$) toward a targeted area for the second liquid ($F_2$) on the substrate (S). The present invention also relates to a method for applying at least two kinds of liquid onto respective targeted areas of a substrate (S).

16 Claims, 6 Drawing Sheets

(51) Int. Cl.
*B05B 12/04* (2006.01)
*A61F 7/00* (2006.01)
*A61Q 19/00* (2006.01)

(52) U.S. Cl.
CPC .. *A45D 2200/057* (2013.01); *A45D 2200/058* (2013.01); *A61F 2007/0003* (2013.01); *A61Q 19/00* (2013.01)

(56) References Cited

U.S. PATENT DOCUMENTS

| | | | |
|---|---|---|---|
| 8,020,315 B2* | 9/2011 | Nishimura | H01L 21/67034 34/350 |
| 2002/0024570 A1 | 2/2002 | Winthrop et al. | |
| 2003/0186826 A1* | 10/2003 | Eccard | C11D 11/0058 510/130 |
| 2004/0012655 A1 | 1/2004 | Thielman et al. | |
| 2006/0104931 A1 | 5/2006 | Fukutome et al. | |
| 2008/0143766 A1* | 6/2008 | Hawkins | B41J 2/03 347/11 |
| 2008/0231669 A1* | 9/2008 | Brost | B41J 2/03 347/75 |
| 2010/0191314 A1 | 7/2010 | Young | |
| 2011/0143550 A1* | 6/2011 | Saito | H01L 21/68728 438/750 |
| 2011/0250103 A1* | 10/2011 | McCarthy | B05B 12/04 422/256 |
| 2016/0270954 A1 | 9/2016 | Young | |

FOREIGN PATENT DOCUMENTS

| | | |
|---|---|---|
| JP | 2015-217378 A | 12/2015 |
| JP | 2018-122225 A | 8/2018 |
| WO | 86/07310 A1 | 12/1986 |
| WO | 2011/146321 A2 | 11/2011 |
| WO | 2015/027055 A1 | 2/2015 |
| WO | 2015/097207 A1 | 7/2015 |
| WO | 2015/140283 A1 | 11/2015 |

OTHER PUBLICATIONS

Machine Generated English Translation of the claims of CN101933890. Published Jan. 5, 2011. (Year: 2011).*

Machine Generated English Translation of the specification of CN101933890. Published Jan. 5, 2011. (Year: 2011).*

Notice of Reasons for Rejection dated Jan. 12, 2021 issued in corresponding Japanese Application No. JP2017-070549, filed on Mar. 31, 2017, 9 pages.

International Search Report and Written Opinion dated May 8, 2018, issued in corresponding International Application No. PCT/JP2018/004102, filed Jan. 31, 2018, 12 pages.

First Chinese Office Action as dated Jul. 26, 2021, issued in corresponding Chinese Application No. 201880015188.3, filed Jan. 31, 2018, 17 pages.

* cited by examiner

70% Speed; 150 μm Nozzle; 76.2 DPI Picture

*FIG. 6*

50% Speed; 150 μm Nozzle; 1.5 Bar Pressure

SYSTEM FOR APPLYING AT LEAST TWO KINDS OF LIQUID ONTO RESPECTIVE TARGETED AREAS OF A SUBSTRATE AND METHOD THEREFOR

TECHNICAL FIELD

The present invention relates to a system and a method for applying at least two kinds of liquid, in particular fluid formulas including cosmetic formulas, onto respective targeted areas of a substrate to, for example, form a facial mask, etc. The present invention further relates to a product produced by such a system and method.

BACKGROUND ART

The skin care required for a user's face varies from region to region of the user, and the care needed for these different regions is different. For example, the T-zone of the skin tends to be oilier than the U-zone of the skin, and therefore the skin care compositions needed for these two zones of the face are different from each other. Another example is the zone around eyes and the remaining zones of the face, both of which need different skin treatments.

It is quite apparent that different topical compositions are required in different skin zones. However, it is not convenient for users to handle several distinct cosmetic product compositions. In other words, applying different cosmetic compositions in appropriate quantities at different zones may be difficult. Therefore, there is a need for a single product which is composed of multiple cosmetic compositions. A substrate-based cosmetic product comprising different cosmetic formulas for targeted zones may be a solution for such a multifunctional product.

Facial masks, patches, and wipes are the most popular substrate-based cosmetic products. Herein, a "substrate-based cosmetic product" refers to a cosmetic product in which a substrate is impregnated with a liquid cosmetic. The level of impregnation in such products varies from product to product. In general, in the case of a facial mask, the level of impregnation is 15 grams to 40 grams per mask sheet, while in the case of wipes, it is 3 grams to 6 grams per wipe sheet.

Thus, there is a need to develop a system which is able to apply sufficient quantities of different cosmetic formulas on respective targeted areas of a substrate without any mixing of these cosmetic formulas.

Prior art related to the present invention is disclosed in the following publications.

US2006/0104931A1 proposes a cosmetic treatment article, more specifically a face mask composed of different gel formulas. However, US2006/0104931A1 does not disclose a system which is able to apply different gel formulas on respective targeted areas of the mask. Furthermore, since the formulas are in gel form, transfer of the formulas to the skin is limited.

US2010/0191314A1 describes a temperature-controlled facial mask with area-specific treatments, wherein the treatments or formulas are sandwiched between two layers of substrate. These formulas can be applied on targeted zones of the substrates by any depiction technique such as lithography, screen printing, ink jet printing, etc. However, US2010/0191314A1 does not describe how to achieve sufficient quantities of formula deposition on the substrates with these techniques.

WO2011/146321A2 describes a method and system for automatic or manual evaluation to provide targeted and individualized delivery of cosmetic actives in a mask or patch form. WO2011/146321A2 proposes using a heatless printing system so that compositions can be printed on a substrate without decomposition. However, WO2011/146321A2 does not describe how to achieve sufficient quantities of formula printing on the substrate.

None of the above publications describes the amount of formula required to be printed on a substrate so that it can be used as a facial mask/patch. Furthermore, these publications also do not describe how to make discrete regions on a substrate so that the mixing of different formulas can be avoided.

In order to eliminate the mixing of two adjacent formulas on a substrate, application of different cosmetic compositions on a substrate in a dry stage has already been proposed in WO2015/140283A1. However, the limitation of utilizing such a substrate-based product is that high amount of polyols or oils cannot be used in such a product since they cannot completely dry. Therefore, such a product does not have the same sensory experience for the user as the packed masks currently sold on the market.

Furthermore, selection of compositions so as to ensure that two successive wet formulas do not mix on a substrate has also been proposed in WO2015/097207A1. However, this prior art still suffers from the disadvantage of requiring a system which can impregnate the different regions with sufficient quantities of the formulas.

DISCLOSURE OF THE INVENTION

In view of the above, an object of the present invention is to provide new solutions for applying sufficient amounts of at least two kinds of liquid, in particular fluid formulas, onto respective targeted areas of a substrate.

In order to achieve the above object, the present invention provides the following: a system for applying at least two kinds of liquid onto respective targeted areas of a substrate, the system including: a first storage unit that accommodates a first liquid and is configured to be capable of causing pressure of a pressured gas to act on the first liquid; a second storage unit that accommodates a second liquid and is configured to be capable of causing pressure of a pressured gas to act on the second liquid; a first applicator that is fluidly connected to the first storage unit, wherein the first applicator comprises at least one nozzle disposed so as to face the substrate, and wherein the first applicator is configured to be capable of spraying the first liquid within the first storage unit from the nozzle toward the substrate by the action of the pressure of the pressured gas; a second applicator that is fluidly connected to the second storage unit, wherein the second applicator comprises at least one nozzle disposed so as to face the substrate, and wherein the second applicator is configured to be capable of spraying the second liquid within the second storage unit from the nozzle toward the substrate by the action of the pressure of the pressured gas; and a controller that is operatively connected to at least the first and second applicator, wherein the controller is configured to be capable of individually controlling a spraying operation of the first and second applicator so that the first applicator sprays the first liquid toward a targeted area for the first liquid on the substrate and the second applicator sprays the second liquid toward a targeted area for the second liquid on the substrate. In particular, in order to achieve the above object, the present invention provides the following: a system for applying at least two kinds of liquid onto respective targeted areas of a substrate, the system including: a first storage unit that accommodates a first liquid; a second storage unit that accommodates a second liquid; a pressured gas supply unit that is fluidly connected to at least the first storage unit and the second storage unit, wherein the pressured gas supply unit is configured to be capable of causing pressure of a pressured gas to act on at least the first and second liquids within the storage unit; a first applicator that is fluidly connected to the first storage unit, wherein the first applicator includes at least one nozzle disposed so as to face the substrate, and wherein the first applicator is configured to be capable of spraying the first liquid within the first storage unit from the nozzle toward the substrate by the action of the pressured gas from the pressured gas supply unit; a second applicator that is fluidly connected to the second storage unit, wherein the second applicator includes at least one nozzle disposed so as to face the substrate, and wherein the second applicator is configured to be capable of spraying the second liquid within the second storage unit from the nozzle toward the substrate by the action of the pressured gas from the pressured gas supply unit; and a controller that is operatively connected to at least the first and second applicator, wherein the controller is configured to be capable of individually controlling a spraying operation of the first and second applicator so that the first applicator sprays the first liquid toward a targeted area for the first liquid on the substrate and the second applicator sprays the second liquid toward a targeted area for the second liquid on the substrate. The present invention further provides a method for applying at least two kinds of liquid onto respective targeted areas of a substrate, the method including: providing at least a first liquid and a second liquid; applying the first liquid to a targeted area for the first liquid on the substrate by an action of a pressured gas; and applying the second liquid to a targeted area for the second liquid on the substrate by an action of a pressured gas, wherein the application of the first liquid and the application of the second liquid are conducted in a coordinated manner. The present invention still further provides a method for applying at least two kinds of liquid onto respective targeted areas of a substrate, using the system stated above, the method including: providing a first liquid from the first storage unit; providing a second liquid from the second storage unit; applying the first liquid to a targeted area for the first liquid on the substrate by an action of the pressured gas, using the first applicator; and applying the second liquid to a targeted area for the second liquid on the substrate by the action of the pressured gas, using the second applicator; wherein the application of the first liquid and the application of the second liquid are conducted in a coordinated manner by the controller. In addition, the present invention provides a product produced by applying at least two kinds of liquid onto respective targeted areas of a substrate, using the system or method stated above.

According to the system and method of the present invention, at least two kinds of liquid are applied by the action of a pressured gas onto the respective targeted areas of the substrate. Thus, according to the present invention, the liquids can be applied onto the respective targeted areas of the substrate in considerably greater amounts per unit time compared to methods such as lithography, screen printing, ink jet printing, etc. As a result, substrate-based wet products, in which sufficient amounts of at least two kinds of liquid have been applied onto individual targeted areas of a substrate, can be obtained efficiently in a short amount of time. Products obtained thereby may be immediately placed on the surface of the body of a user for the purpose of targeted treatment. Alternatively, such products may be semi dried so as to be packable without any mixing of the different liquids.

In a preferred aspect of the present invention, the first applicator includes at least one first valve that corresponds to the nozzle and is operable to be opened/closed so as to permit or block the flow of the first liquid to the nozzle, and the second applicator includes at least one second valve that corresponds to the nozzle and is operable to be opened/ closed so as to permit or block the flow of the second liquid to the nozzle, wherein the controller is configured to be capable of individually controlling an opening/closing operation of the first and second valves.

In a preferred aspect of the present invention, the system further includes a conveyor for conveying the substrate along a direction parallel to a surface of the substrate, wherein the controller is configured to be capable of simultaneously controlling the spraying operation of the first and second applicator and a conveying operation of the conveyor so that the first and second applicator and the conveyor operate in a coordinated manner.

In a preferred aspect of the present invention, the first and second applicator are configured to be capable of reciprocal movement in a direction orthogonal to a conveying direction of the substrate, and the controller is configured to be capable of simultaneously controlling the spraying operation and the reciprocal movement of the first and second applicator and the conveying operation of the conveyor so that the first and second applicator and the conveyor operate in a coordinated manner.

In a preferred aspect of the present invention, the system further includes a third storage unit for accommodating a third liquid, wherein the pressured gas supply unit is further fluidly connected to the third storage unit; and a third applicator that is fluidly connected to the third storage unit, wherein the third applicator includes at least one nozzle disposed so as to face the substrate, and wherein the third applicator is configured to be capable of spraying the third liquid within the third storage unit from the nozzle toward the substrate by the action of the pressured gas from the pressured gas supply unit, wherein the controller is configured to be capable of individually controlling the spraying operation of the first to third applicator so that the third applicator sprays the third liquid toward a boundary area between the targeted area for the first liquid and the targeted area for the second liquid on the substrate. According to this aspect, if, for example, a binder, preferably a quick-drying binder, is used as the third liquid, mixing of the first and second liquids in the boundary between the two liquids after application can be reliably prevented.

In a preferred aspect of the present invention, the third applicator includes at least one third valve that corresponds to the nozzle and is operable to be opened/closed so as to permit or block the flow of the third liquid to the nozzle, wherein the controller is configured to be capable of individually controlling an opening/closing operation of the first to third valves.

In a preferred aspect of the present invention, the pressured gas supply unit is a compressor and/or a pressured gas storage tank. Further, it is particularly preferable to use pressured air as the pressured gas.

The substrate may be a sheet-like substrate of a cosmetic article, for example a facial mask, facial patch, or facial wipe.

In a preferred aspect of the product according to the present invention, the application level per unit area of the liquids may be at least 300 grams/m². Furthermore, in a preferred aspect, the product may be a cosmetic article such as a facial mask.

BRIEF DESCRIPTION OF THE DRAWINGS

Non-limiting and representative embodiments of the present invention will now be explained in detail below referring to the attached drawings.

DETAILED DESCRIPTION OF EMBODIMENTS

An embodiment of the present invention will now be explained referring to FIGS. 1 to 4. In the embodiment explained below, three kinds of liquid, i.e. two fluid cosmetic formulas and one binder, will be used. However, the present invention may be similarly carried out using only two fluid formulas without using a binder, or using three or more kinds of liquid with or without using a binder.

Figure 1:
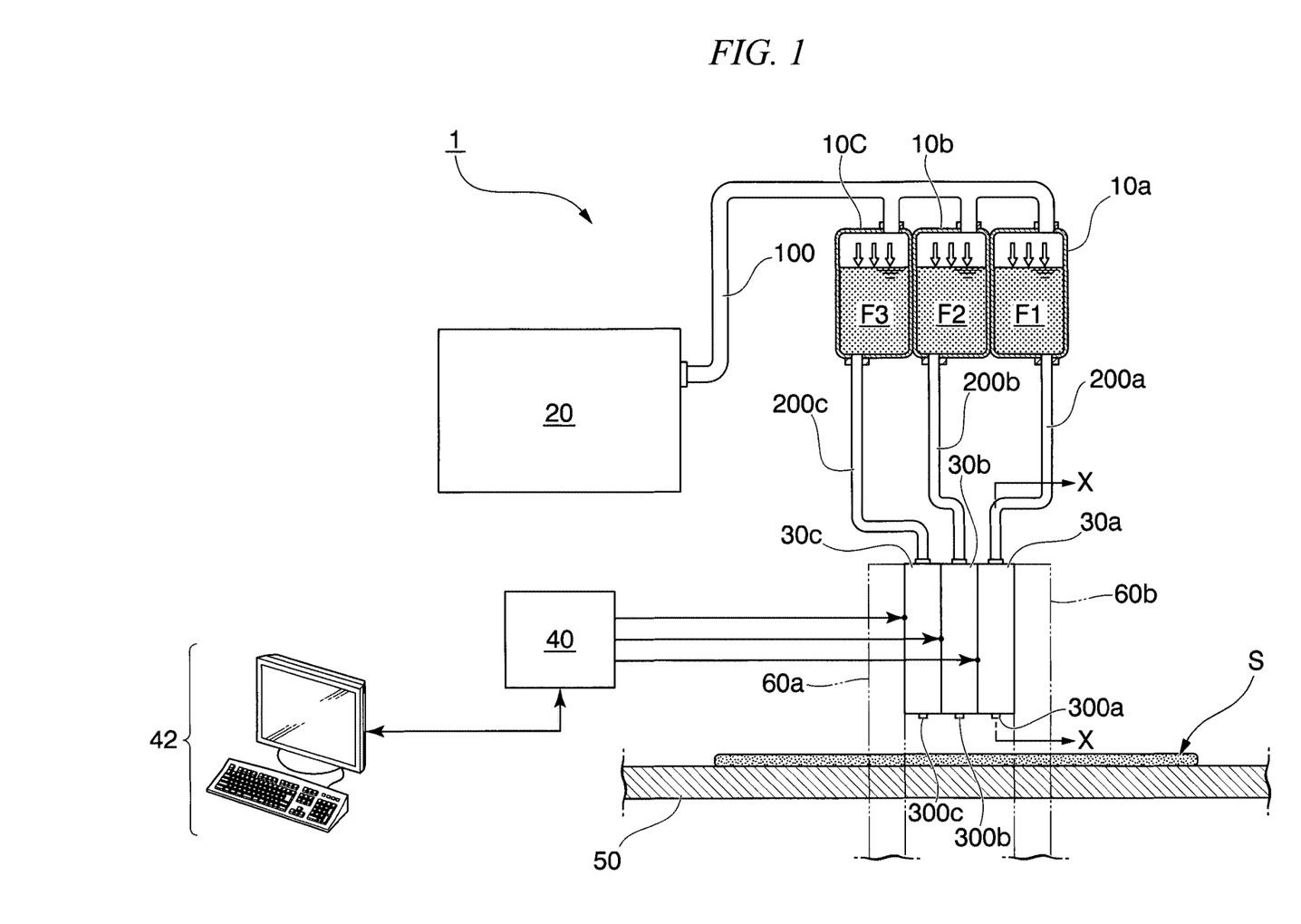
FIG. 1 is a schematic diagram of a system for applying two cosmetic formulas and a binder onto respective targeted areas of a substrate according to one embodiment of the present invention.

The system that is roughly illustrated and indicated by reference numeral 1 in FIG. 1 is used for applying two cosmetic formulas and one binder onto separated targeted areas (to be explained in detail below) of a substrate S. In the present embodiment, the substrate S is a sheet-like substrate of a cosmetic article, particularly a facial mask. The substrate S is manufactured from, for example, a nonwoven sheet consisting of cellulose, and more specifically a 100% viscose spun lace nonwoven sheet of 50 gsm (grams/m²). The substrate S can be any shape and size, one of examples can be substrate S in the shape of facial mask. Using the system 1, the two cosmetic formulas (a serum, a lotion, etc.) are applied onto (or impregnated into) the substrate S, and thereby a wet facial mask is obtained. Normally, elliptical openings are formed at positions corresponding to the eyes and mouth of a user of the substrate S serving as the facial mask. Further, a U-shaped slit is formed at a position corresponding to the nose of the user (refer to FIG. 4).

The system 1 includes first and second storage tanks 10a, 10b that respectively accommodate a first formula $F_1$ and a second formula $F_2$ which are made of different components, and a third storage tank 10c that accommodates a quick-drying binder $F_3$. The tanks 10a, 10b, and 10c may be in a separated state, or may be integrated as shown in the drawings. The tanks 10a, 10b, and 10c also may be installed at positions separated from the application units (i.e., the applicators) to be explained later, or may be integrated with their respective application units.

The system 1 also includes a pressured gas supply unit 20 that is fluidly connected to the first to third tanks 10a to 10c via a flexible tube 100. The unit 20 is configured to be capable of causing the pressure of a pressured gas to act on the first and second formulas $F_1$ and $F_2$ and the binder $F_3$ within the tanks 10a to 10c. Therefore, during operation of the system 1, the pressure of the pressured gas acts as shown by the arrows in FIG. 1 on the liquid surfaces of the first and second formulas $F_1$ and $F_2$ and the binder $F_3$.

In the present embodiment, the pressured gas supply unit 20 is a compressor. However, alternatively, a pressured gas storage tank may also be used. Further, in the present embodiment, the pressured gas is pressured air. However, alternatively, another gas that is not reactive with the formulas and binder used in the system 1 may also be used. Although not illustrated, the unit 20 includes a sensor that detects the pressure of the pressured gas to be supplied to the first to third tanks 10a to 10c. Information obtained from this sensor may be input into the control unit to be explained later as an operation parameter.

Figure 2A:
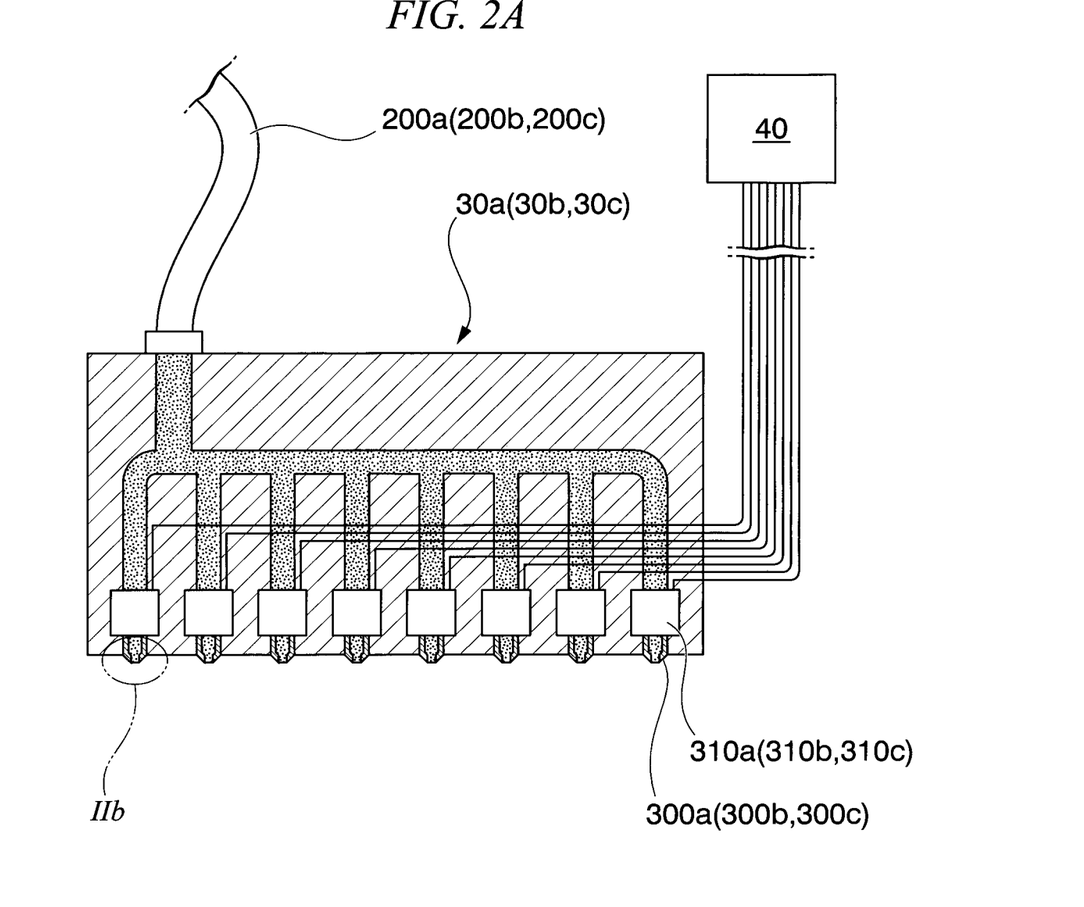
FIG. 2A is a cross-sectional view of an application unit of the system along line X-X in FIG. 1.
Figure 2B:
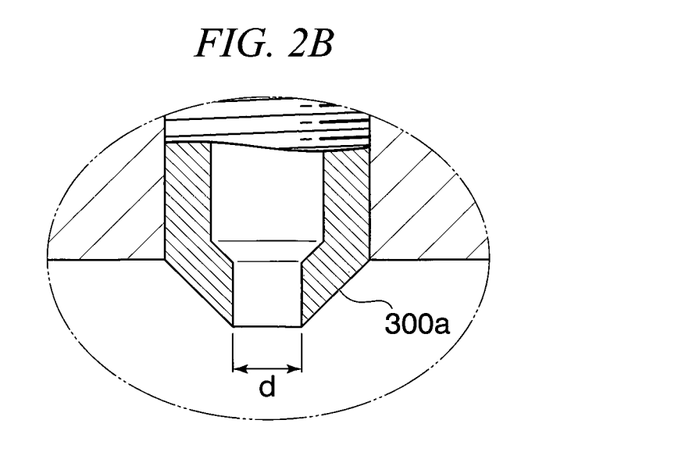
FIG. 2B is an enlarged view of IIb portion in FIG. 2A.

The system 1 also includes first to third application units 30a, 30b, 30c that are fluidly connected to the first to third storage tanks 10a to 10c via flexible tubes 200a, 200b, 200c. In the present embodiment, the first to third application units 30a to 30c are joined to each other. As can be understood from FIGS. 2 and 3, the first application unit 30a includes a plurality of nozzles 300a that are disposed in one row, particularly one row in a direction orthogonal to the conveying direction of the substrate S, so as to face the substrate S. The first application unit 30a is configured to be capable of spraying the first formula $F_1$ within the tank 10a from the nozzles 300a toward the substrate S by the action of the pressured gas from the unit 20. The second and third applications units 30b and 30c also have the same structure. The second application unit 30b also includes a plurality of nozzles 300b disposed in one row so as to face the substrate S, and can spray the second formula $F_2$ within the tank 10b from the nozzles 300b toward the substrate S by the action of the pressured gas from the unit 20. The third application unit 30c also includes a plurality of nozzles 300c disposed in one row so as to face the substrate S, and can spray the binder $F_3$ within the tank 10c from the nozzles 300c toward the substrate S by the action of the pressured gas from the unit 20.

In further detail, as is roughly illustrated in FIG. 2A, for example, the first application unit 30a includes a plurality of first valves 310a corresponding to the nozzles 300a. The first valves 310a are operable to be opened/closed so as to permit or block the flow of the first formula $F_1$ from the tank 10a to the nozzles 300a. Opening and closing of these valves are controlled electronically according to signal received from a control unit 40 explained below. As can be easily understood from FIG. 2A, the second application unit 30b also includes a plurality of second valves 310b corresponding to the nozzles 300b. The second valves 310b are operable to be opened/closed so as to permit or block the flow of the second formula $F_2$ from the tank 10b to the nozzles 300b. Further, the third application unit 30c also includes a plurality of third valves 310c corresponding to the nozzles 300c. The third valves 310c are operable to be opened/closed so as to permit or block the flow of the binder $F_3$ from the tank 10c to the nozzles 300c.

In the present embodiment, a single pressured gas supply unit 20 is shared by the application units 30a to 30c. However, a plurality of pressured gas supply units may be allocated corresponding to each of the application units 30a to 30c. Further, only two application units may be prepared (in the case where only two kinds of fluid formula are used), or four or more application units may be prepared.

The system 1 also includes an electronic control unit (i.e., controller) 40 that is operatively connected to the first to third application units 30a to 30c. An input unit 42 is also connected to the control unit 40. The application style of the first and second formulas $F_1$ and $F_2$ and the binder $F_3$ on the substrate S, or in other words a "picture" that is drawn on the substrate S using the first and second formulas $F_1$ and $F_2$ and the binder $F_3$, is input into the control unit 40 using the input unit 42.

Figure 4:
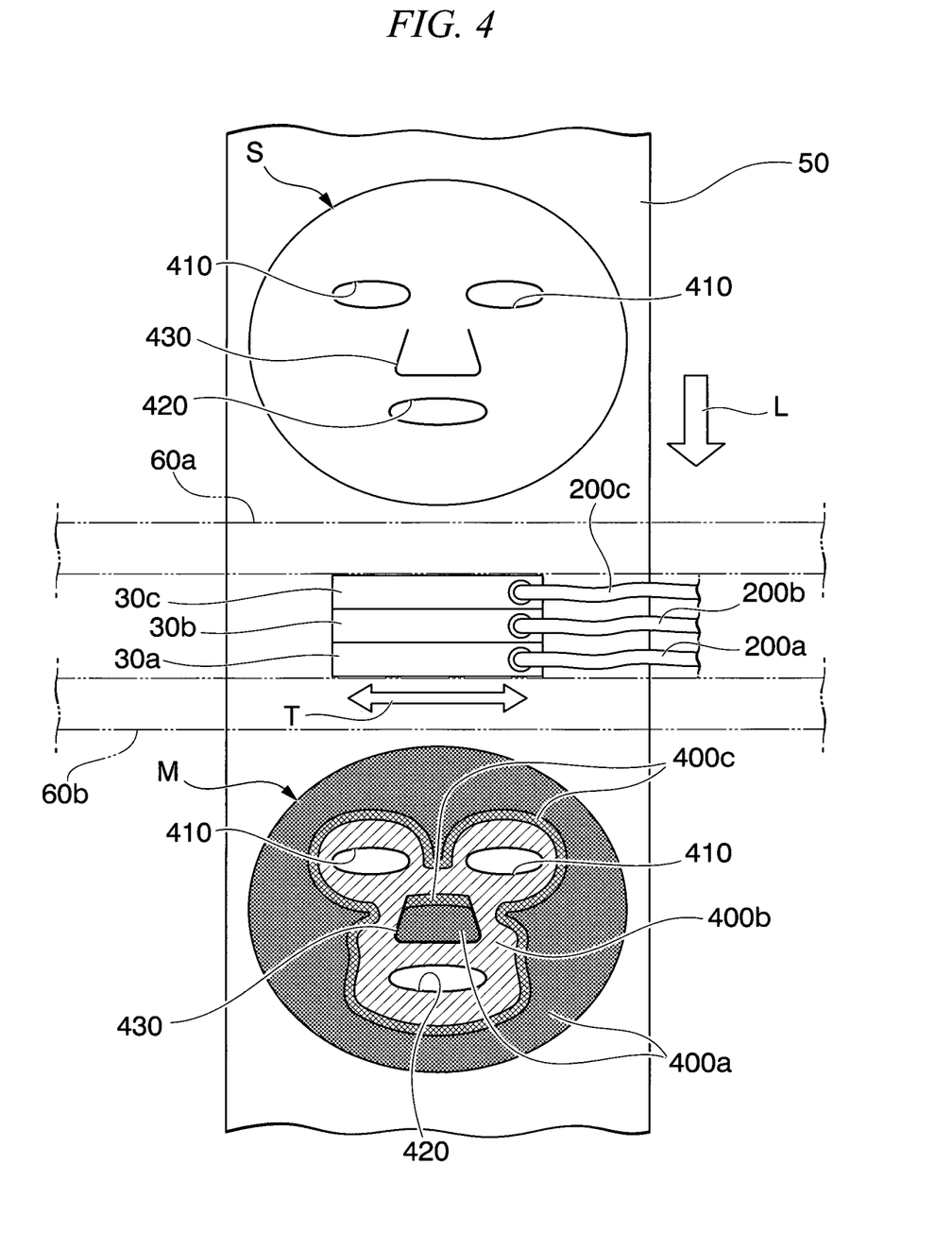
FIG. 4 is a plan view illustrating an application process being executed by the system shown in FIG. 1.

Upon receiving data related to the "picture" from the input unit 42, the control unit 40 is configured to be capable of individually controlling the spraying operation of the first to third application units 30a to 30c based on the data. In more accurate terms, the control unit 40 is configured to be capable of individually controlling the opening/closing operation of the first to third valves 310a to 310c. For example, the first application unit 30a sprays the first formula $F_1$ toward a targeted area for the first formula $F_1$ on the substrate S under the control of the control unit 40. The targeted area for the first formula $F_1$ corresponds to a region 400a indicated using dots of the substrate S after being subjected to the application process, i.e. of a facial mask M as shown in FIG. 4. The second application unit 30b also sprays the second formula $F_2$ toward a targeted area for the second formula $F_2$ on the substrate S under the control of the control unit 40. The targeted area for the second formula $F_2$ corresponds to a region 400b indicated using slanted lines of the facial mask M as shown in FIG. 4. Further, the third application unit 30c also sprays the binder $F_3$ toward a boundary area between the targeted area for the first formula $F_1$ and the targeted area for the second formula $F_2$ under the control of the control unit 40. This targeted area corresponds to a region 400c indicated using cross-hatched lines of the facial mask M as shown in FIG. 4.

In the present embodiment, the region 400b for the second formula $F_2$ exists so as to surround the eyes, nose, and mouth of the user. In FIG. 4, the openings in the substrate S corresponding to the eyes and mouth of the user are indicated by reference numerals 410 and 420. The region 400a for the first formula $F_1$ exists so as to surround the region 400b for the second formula $F_2$. A nose flap defined by a U-shaped slit 430 is also the region 400a for the first formula $F_1$. The narrow region 400c for the binder $F_3$ exists between the region 400a and the region 400b excluding the vicinity of the slit 430.

Figure 3:
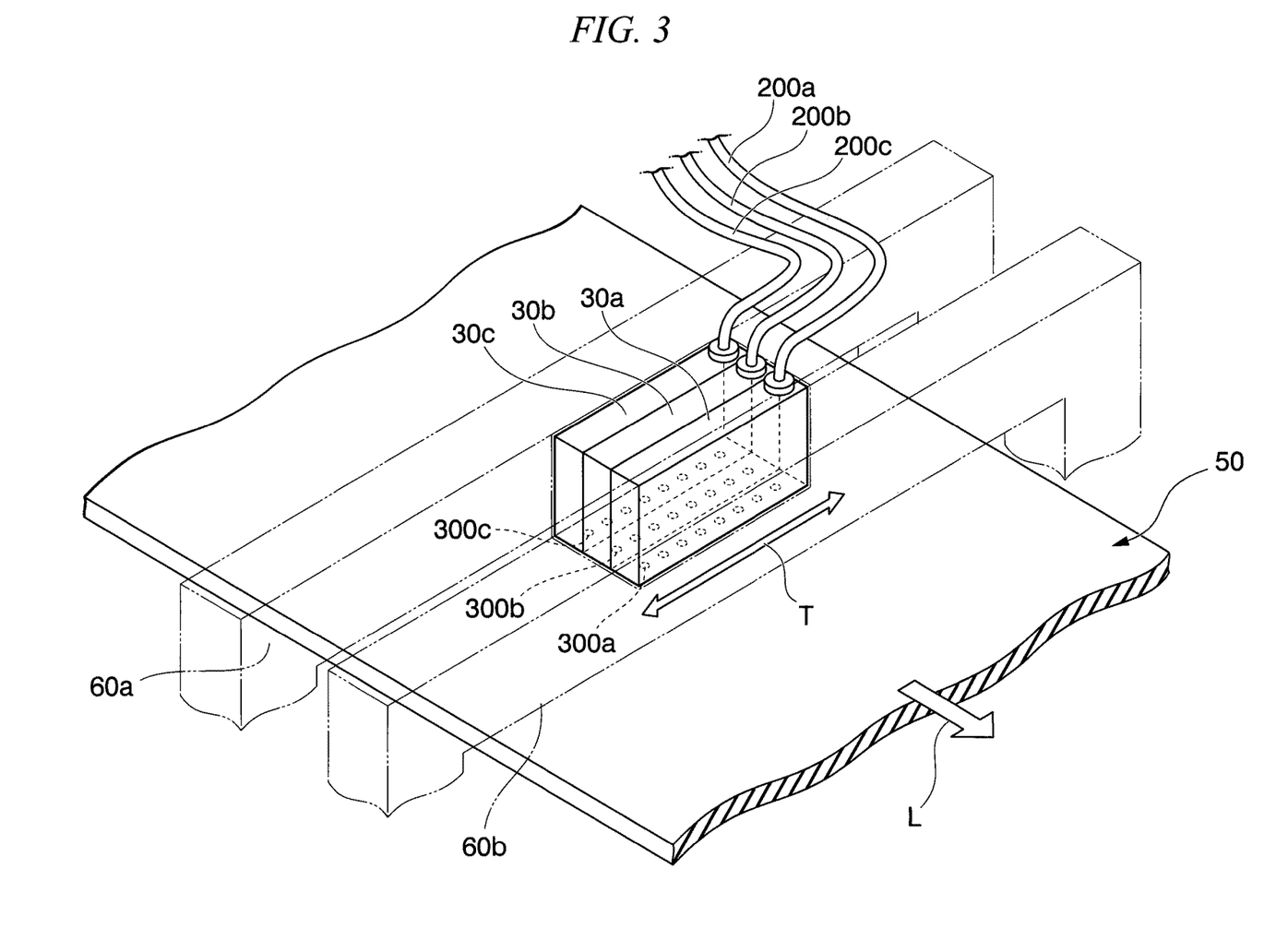
FIG. 3 is a perspective view of the application unit of the system shown in FIG. 1.

The system 1 also includes a conveyer 50, for example a belt conveyer, for conveying the substrate S along a direction parallel to the surface of the substrate S, i.e. in a direction L indicated in FIGS. 3 and 4. Further, the first to third application units 30a to 30c are displaceably supported by a pair of guide rails 60a, 60b in a state in which the units 30a to 30c are sandwiched between the pair of guide rails 60a, 60b. In other words, the first to third application units 30a to 30c are configured to be capable of reciprocal movement along the guide rails 60a, 60b at a high speed in a direction T orthogonal to the conveying direction L of the substrate. The high-speed reciprocal movement of the units 30a to 30c is realized using, for example, a linear actuator (not illustrated). In other embodiments, the first to third application units 30a to 30c do not have to be fixed in position, or the conveyer 50 does not have to be used.

On the basis of the data related to the "picture", the control unit 40 simultaneously controls the application operation and the reciprocal movement of the application units 30a to 30c as well as the conveying operation of the conveyer 50 so that the application units 30a to 30c and the conveyer 50 operate in a coordinated manner. As a result, while the substrate S passes under the application units 30a to 30c, the first and second formulas $F_1$ and $F_2$ and the binder $F_3$ are respectively applied onto their designated areas. In FIG. 4, the substrate S which has not yet been subjected to the application process is shown on the upstream side of the application units 30a to 30c, whereas the substrate S in which the application process is complete, i.e. the facial mask M, is shown on the downstream side of the application units 30a to 30c.

In an alternative embodiment, the pressured gas supply unit 20 is omitted, and instead, the tank 10a is configured to be capable of causing pressure of the pressured gas to act on the first formula $F_1$, and the tank 10b is configured to be capable of causing pressure of the pressured gas to act on the second formula $F_2$.

In the following, referring to FIGS. 5 to 8, an embodiment of a method for applying the two fluid formulas and the binder onto the substrate that is executed using the above-described system will be explained. As an example, the overall surface area of the substrate S to be used is 314 cm$^2$ and it is in shape of face mask with openings for eyes, mouth and slit for nose. The target application amount of the formulas per substrate is 20 grams. Furthermore, in this embodiment, the application level per unit area of the formulas is at least 300 grams/m$^2$.

During execution of this application method, first, the first and second formulas $F_1$ and $F_2$ and the binder $F_3$ are provided. As an example, as the first and second formulas $F_1$ and $F_2$, formulas including the components shown below in Table 1 may be used.

TABLE 1

| Ingredient | Formula $F_1$ | Formula $F_2$ |
| --- | --- | --- |
| Water | 88.94% | 88.94% |
| Glycerin | 5% | 5% |
| Butylene Glycol | 3% | 3% |
| Pentylene Glycol | 2% | 2% |
| Phenoxyethanol | 0.5% | 0.5% |
| Blue Color | 0.06% | 0% |
| Hyaluronic Acid | 0.5% | 0% |
| Yellow Color | 0% | 0.06% |
| Ellagic Acid | 0% | 0.5% |

Next, the substrate S is set on the conveyer 50. After setting the substrate S, the conveyer 50 and the first to third application units 30a to 30c are operated by the control unit 40. Therein, the first formula $F_1$ is applied toward the targeted area for the first formula $F_1$ on the substrate S by the action of the pressured gas. The second formula $F_2$ is also applied toward the targeted area for the second formula $F_2$ on the substrate S by the action of the pressured gas. Further, the binder $F_3$ is also applied toward a boundary area between the targeted area for the first formula $F_1$ and the targeted area for the second formula $F_2$ by the action of the pressured gas. The application operation of the first and second formulas $F_1$ and $F_2$ and the binder $F_3$, the reciprocal movement of the application units 30a to 30c, and the conveying of the substrate S by the conveyer 50 are executed in a coordinated manner under the control of the control unit 40. As a result, when the substrate S has completely passed under the first to third application units 30a to 30c, a final product, i.e. the facial mask M, in which the first formula $F_1$ has been applied to the region 400a, the second formula $F_2$ has been applied to the region 400b, and the binder $F_3$ has been applied to the region 400c, is obtained as shown in FIG. 4.

According to this application method, the conveyer 50 and the first to third application units 30a to 30c are made to operate in a coordinated manner under the control of the control unit 40, and thereby sufficient amounts of the first and second formulas $F_1$ and $F_2$ and the binder $F_3$ are respectively applied to the regions 400a to 400c. In the facial mask M obtained in this way, the applied first and second formulas $F_1$ and $F_2$ are completely separated by the dried binder $F_3$. Therefore, mixing of the first and second formulas $F_1$ and $F_2$ does not readily occur over a long period of time, and the facial mask can be used even several days after the manufacture thereof.

In the case that the mask manufactured as described above is intended to be used immediately, the application of the binder can be eliminated. In this case, the system 1 does not need to include the third application unit 30c. Further, the mask manufactured as described above may be immediately dried, either completely or partially, using hot air or the like at a temperature which does not affect the stability of the formulas $F_1$ and $F_2$, for example 70° C. In this case, the entire water composition is dried out, and as a result only polyols, oils, and active ingredients remain in the mask. The dried mask is thereafter accommodated/packed in a sachet. The mask subjected to this treatment is wetted with water by a user immediately before use.

In the above-described embodiments, the amounts of the liquids to be applied onto the substrate S, particularly the amounts of the first formula $F_1$ and the second formula $F_2$, depend on the following Parameters 1 to 4:
1. the gas pressure;
2. the resolution of the "picture" to be drawn on the substrate with the formulas;
3. the size of the nozzles (the diameter of the port of the nozzles); and
4. the speed for conveying the substrate.

By modifying these Parameters 1 to 4, the application amounts of the first formula $F_1$ and the second formula $F_2$ on the substrate S are adjusted. FIGS. 5 to 8 illustrate the relationships between these parameters and the application level per unit area of the formulas [gsm], as well as the relationship between the application level of the formulas and the application amount [grams].

Figure 5:
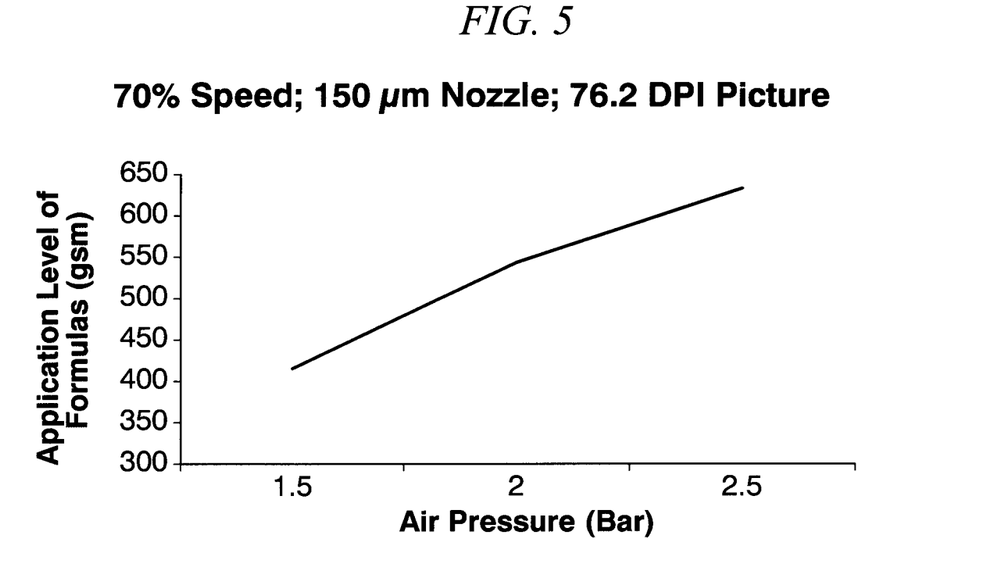
FIG. 5 is a line graph illustrating the relationship between the application level per unit area of the formulas and the air pressure.

The line graph in FIG. 5 illustrates the relationship between the application level per unit area of the formulas [gsm] and the air pressure [bar]. Herein, the conveying speed of the substrate is 70% of the maximum value, the nozzle size, i.e. the diameter of the port of the nozzles (indicated as "d" in FIG. 2B), is 150 µm, and the resolution of the "picture" is 76.2 DPI. From FIG. 5, it can be understood that the application level of the formulas increases as the air pressure increases.

Figure 6:
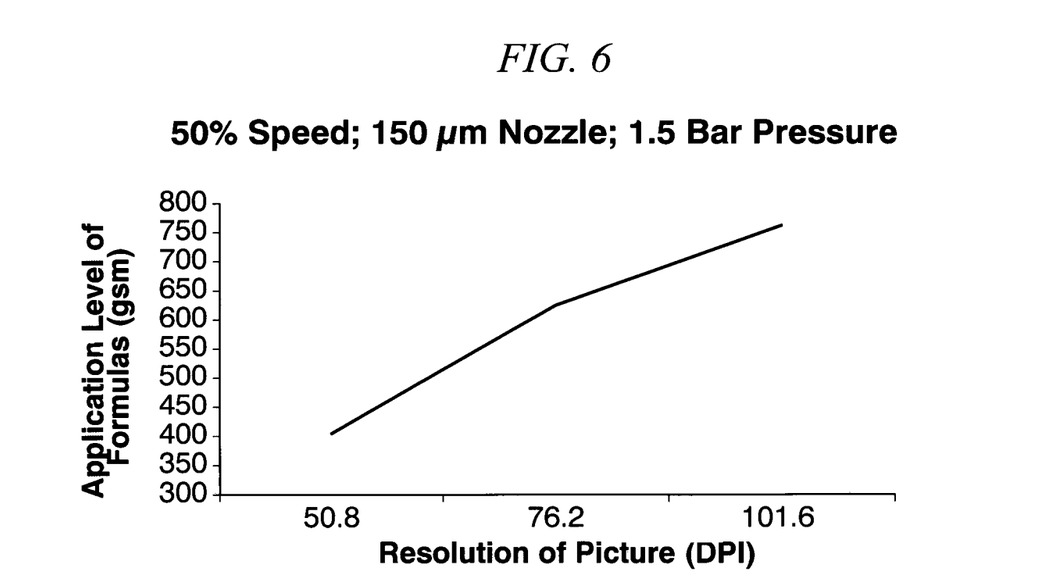
FIG. 6 is a line graph illustrating the relationship between the application level per unit area of the formulas and the resolution of a "picture" to be drawn on the substrate with the formulas.

The line graph in FIG. 6 illustrates the relationship between the application level per unit area of the formulas [gsm] and the resolution of the "picture" to be drawn on the substrate with the formulas [DPI]. Herein, the conveying speed of the substrate is 50% of the maximum value, the nozzle size is 150 µm, and the air pressure is 1.5 bar. From FIG. 6, it can be understood that the application level of the formulas increases as the resolution of the "picture" increases.

Figure 7:
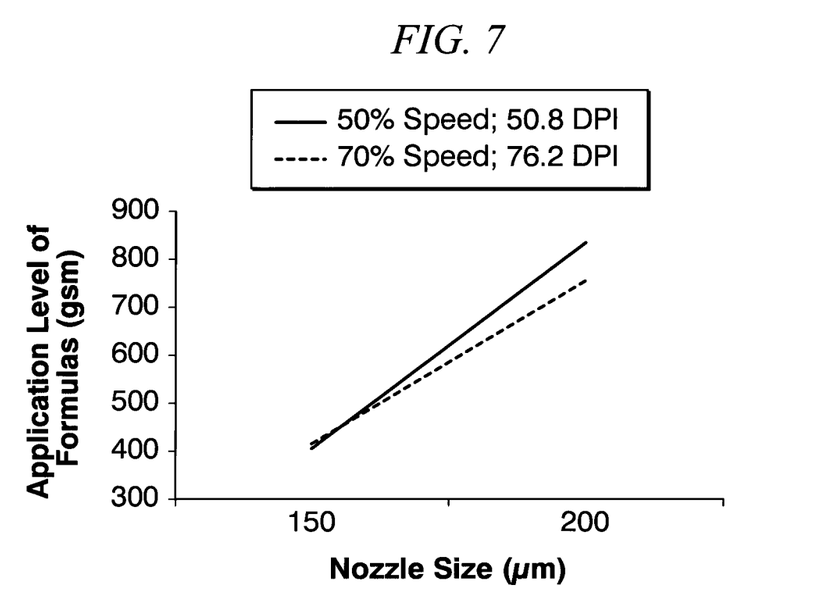
FIG. 7 is a line graph illustrating the relationship between the application level per unit area of the formulas and the nozzle size.

The line graph in FIG. 7 illustrates the relationship between the application level per unit area of the formulas [gsm] and the size of the nozzle [µm]. In FIG. 7, the solid line indicates a case in which the conveying speed of the substrate is 50% of the maximum value and the resolution of the "picture" is 50.8 DPI, whereas the dashed line indicates a case in which the conveying speed of the substrate is 70% of the maximum value and the resolution of the "picture" is 76.2 DPI. From FIG. 7, it can be understood that the application level of the formulas increases as the nozzle size increases.

Figure 8:
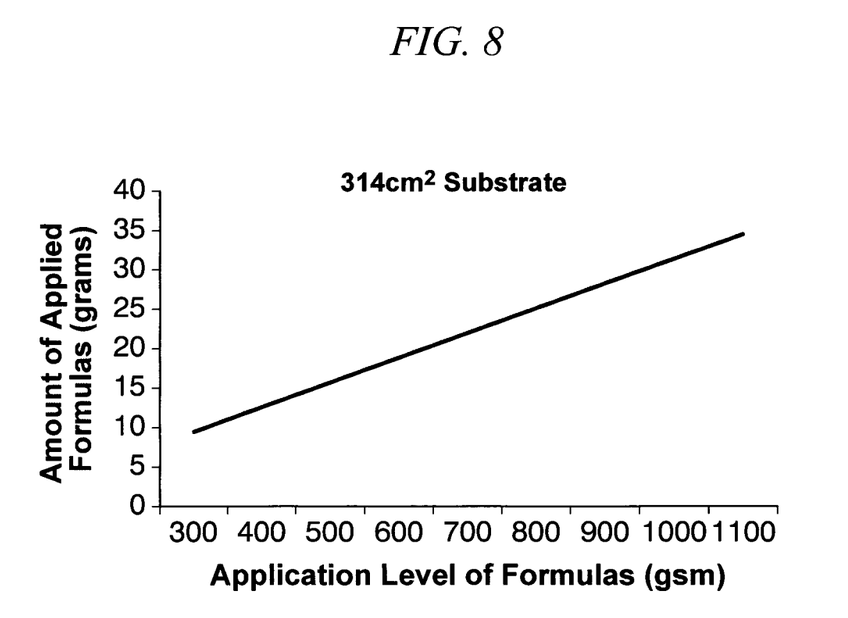
FIG. 8 is a line graph illustrating the relationship between the application amount of the formulas on the substrate and the application level per unit area of the formulas.

The line graph in FIG. 8 illustrates the relationship between the application amount of the formulas on the substrate [grams] and the application level per unit area of the formulas [gsm]. From FIG. 8, it can be understood that when the overall surface area of the substrate S is 314 cm$^2$, the target application amount of 20 grams is achieved by an application level of about 634 [gsm].

Preferred embodiments of the present invention have been explained above referring to the drawings. However, the present invention is not limited to these embodiments, and various modifications and changes may be made to the above-described embodiments without deviating from the gist and scope of the present invention, and such modifications and changes are included in the scope of the present invention.

The invention claimed is:

1. A system (1) for applying at least two kinds of liquid onto respective targeted areas of a substrate (S), said system (1) comprising:
   a first storage unit (10a) that accommodates a first liquid ($F_1$), wherein the first liquid is a first fluid formula, and is configured to be capable of causing pressure of a pressured gas to act on the first liquid ($F_1$);
   a second storage unit (10b) that accommodates a second liquid ($F_2$), wherein the second liquid is a second fluid formula, and is configured to be capable of causing pressure of a pressured gas to act on the second liquid ($F_2$);
   a third storage unit (10c) for accommodating a third liquid ($F_3$), wherein the third liquid is a binder for separating the first liquid ($F_r$) and the second liquid ($F_2$) from each other;
   a first applicator (30a) that is fluidly connected to the first storage unit (10a), wherein the first applicator (30a) comprises at least one nozzle (300a) disposed so as to face the substrate (S), and wherein the first applicator (30a) is configured to be capable of spraying the first liquid ($F_1$) within the first storage unit (10a) from the nozzle (300a) toward the substrate (S) by the action of the pressure of the pressured gas;
   a second applicator (30b) that is fluidly connected to the second storage unit (10b), wherein the second applicator (30b) comprises at least one nozzle (300b) disposed so as to face the substrate (S), and wherein the second applicator (30b) is configured to be capable of spraying the second liquid ($F_2$) within the second storage unit (10b) from the nozzle (300b) toward the substrate (S) by the action of the pressure of the pressured gas;
   a third applicator (30c) that is fluidly connected to the third storage unit (10c), wherein the third applicator (30c) comprises at least on nozzle (300c) disposed so as to face the substrate (S) and wherein the third applicator (30c) is configured to be capable of spraying the third liquid ($F_3$) within the third storage unit (10c) from the nozzle (300c) toward the substrate (S) by the action of the pressured gas; and a controller (40) that is operatively connected to at least the first and second applicator (30a, 30b), wherein the controller (40) is configured to be capable of individually controlling a spraying operation of the first and second applicator (30a, 30b) so that the first applicator (30a) sprays the first liquid ($F_1$) toward a targeted area for the first liquid ($F_1$) on the substrate (S) and the second applicator (30b) sprays the second liquid ($F_2$) toward a targeted area for the second liquid ($F_2$) on the substrate (S), wherein the system (1) further comprising a conveyor (50) for conveying the substrate (S) along a direction parallel to a surface of the substrate (S), wherein the conveyer (50) is configured such that the substrate (S) is set on the conveyer (50), wherein the controller (40) is configured to be capable of simultaneously controlling the spraying operation of the first and second applicator (30a, 30b) and a conveying operation of the conveyor (50) so that the first and second applicator (30a, 30b) and the conveyor (50) operate in a coordinated manner, and wherein amounts of the first liquid ($F_1$) and the second liquid ($F_2$) to be applied on the substrate (S) depend on parameters including:
  a gas pressure;
  a resolution of a picture to be drawn on the substrate (S) with the liquids,
  a diameter of a port of the nozzle (300b), and
  a speed for conveying the substrate (S); and wherein the application amounts of the first liquid ($F_1$) and the second liquid ($F_2$) on the substrate (S) can be adjusted by modifying the parameters, wherein the first applicator (30a) comprises at least one first valve (310a) that corresponds to the nozzle (300a) and is operable to be opened/closed so as to permit or block the flow of the first liquid ($F_1$) to the nozzle (300a), wherein the second applicator (30b) comprises at least one second valve (310b) that corresponds to the nozzle (300b) and is operable to be opened and closed so as to permit or block the flow of the second liquid ($F_2$) to the nozzle (300b), wherein the controller (40) is configured to be capable of individually controlling an opening and closing operation of the first and second valves (310a, 310b) and wherein the controller is configured to be capably of individually controlling the spraying operayion of the first to third applicator (30a, 30b, 30c) so that the third applicator (30c) sprays the third liquid ($F_3$) toward a boundary area between the targeted area for the first liquid ($F_1$) and the targeted area for the second liquid ($F_2$) on the substrate (S).

2. A system (1) for applying at least two kinds of liquid onto respective targeted areas of a substrate (S), said system (1) comprising:
  a first storage unit (10a) that accommodates a first liquid ($F_1$), wherein the first liquid is a first fluid formula;
  a second storage unit (10b) that accommodates a second liquid ($F_2$), wherein the second liquid is a second fluid formula;
  a third storage unit (10c) for accommodating a third liquid ($F_3$), wherein the third liquid is a binder for separating the first liquid ($F_1$) and the second liquid ($F_2$) from each other;
  a pressured gas supply unit (20) that is fluidly connected to the first to third storage units (10a, 10b, 10c), wherein the pressured gas supply unit (20) is configured to be capable of causing pressure of a pressured gas to act on the first to third-liquids ($F_1$, $F_2$, $F_3$) within the storage units (10a, 10b, 10c);
  a first applicator (30a) that is fluidly connected to the first storage unit (10a), wherein the first applicator (30a) comprises at least one nozzle (300a) disposed so as to face the substrate (S), and wherein the first applicator (30a) is configured to be capable of spraying the first liquid ($F_1$) within the first storage unit (10a) from the nozzle (300a) toward the substrate (S) by the action of the pressured gas from the pressured gas supply unit (20);
  a second applicator (30b) that is fluidly connected to the second storage unit (10b), wherein the second applicator (30b) comprises at least one nozzle (300b) disposed so as to face the substrate (S), and wherein the second applicator (30b) is configured to be capable of spraying the second liquid ($F_2$) within the second storage unit (10b) from the nozzle (300b) toward the substrate (S) by the action of the pressured gas from the pressured gas supply unit (20);
  a third applicator (30c) that is fluidly connected to the third storage unit (10c), wherein the third applicator (30c) comprises at least on nozzle (300c) disposed so as to face the substrate (S) and wherein the third applicator (30c) is configured to be capable of spraying the third liquid ($F_3$) within the third storage unit (10c) from the nozzle (300c) toward the substrate (S) by the action of the pressured gas; and
  a controller (40) that is operatively connected to at least the first and second applicator (30a, 30b), wherein the controller (40) is configured to be capable of individually controlling a spraying operation of the first and second applicator (30a, 30b) so that the first applicator (30a) sprays the first liquid ($F_1$) toward a targeted area for the first liquid ($F_1$) on the substrate (S) and the second applicator (30b) sprays the second liquid ($F_2$) toward a targeted area for the second liquid ($F_2$) on the substrate (S), wherein the system (1) further comprises a conveyor (50) for conveying the substrate (S) along a direction parallel to a surface of the substrate (S), wherein the conveyer (50) is configured such that the substrate (S) is set on it, wherein the controller (40) is configured to be capable of simultaneously controlling the spraying operation of the first and second applicator (30a, 30b) and a conveying operation of the conveyor (50) so that the first and second applicator (30a, 30b) and the conveyor (50) operate in a coordinated manner, and wherein amounts of the first liquid ($F_1$) and the second liquid ($F_2$) to be applied on the substrate (S) depend on parameters including:
  a gas pressure;
  a resolution of a picture to be drawn on the substrate (S) with the liquids,
  a diameter of a port of the nozzle (300b), and
  a speed for conveying the substrate (S); and wherein the application amounts of the first liquid ($F_1$) and the second liquid ($F_2$) on the substrate (S) can be adjusted by modifying the parameters, wherein the first applicator (30a) comprises at least one first valve (310a) that corresponds to the nozzle (300a) and is operable to be opened/closed so as to permit or block the flow of the first liquid ($F_1$) to the nozzle (300a), wherein the second applicator (30b) comprises at least one second valve (310b) that corresponds to the nozzle (300b) and is operable to be opened and closed so as to permit or block the flow of the second liquid ($F_2$) to the nozzle (300b), wherein the controller (40) is configured to be capable of individually controlling an opening and closing operation of the first and second valves (310a, 310b) and wherein the controller is configured to be capably of individually controlling the spraying operayion of the first to third applicator (30a, 30b, 30c) so that the third applicator (30c) sprays the third liquid ($F_3$) toward a boundary area between the targeted area for the first liquid ($F_1$) and the targeted area for the second liquid ($F_2$) on the substrate (S).

3. The system (1) according to claim 2, wherein the pressured gas supply unit (20) is a compressor and/or a pressured gas storage tank.

4. A method for applying at least two kinds of liquid onto respective targeted areas of a substrate (S), using the system (1) according to claim 2, said method comprising:
providing a first liquid ($F_1$) from the first storage unit (10a), wherein the first fluid ($F_1$) is a first fluid formula;
providing a second liquid ($F_2$) from the second storage unit (10b), wherein the second fluid ($F_2$) is a second fluid formula;
providing a third fluid ($F_3$), wherein the third fluid ($F_3$) is a binder for separating the first liquid ($F_1$) and the second liquid ($F_3$) from each other from the third storage unit (10c);
applying the first liquid ($F_1$) to a targeted area for the first liquid ($F_1$) on the substrate (S) by an action of the pressured gas, using the first applicator (30a) while conveying the substrate (S) by a conveyor (50) along a direction parallel to a surface of the substrate (S), wherein the conveyer (50) is configured such that the substrate (S) is set on the conveyer (50);
applying the second liquid ($F_2$) to a targeted area for the second liquid ($F_2$) on the substrate (S) by the action of the pressured gas, using the second applicator (30b) while conveying the substrate (S) by the conveyor (50) along the direction parallel to the surface of the substrate (S);
applying the third liquid ($F_3$) to a boundary area between the targeted area for the first liquid ($F_1$) and the targeted area for the second liquid ($F_2$) on the substrate (S) by the action of the pressured gas, using the third applicator (30c) while conveying the substrate (S) by the conveyor (50) along the direction parallel to the surface of the substrate (S),
wherein the application of the first liquid ($F_1$), the application of the second liquid ($F_2$), and the application of the third liquid ($F_3$) and the conveying operation of the conveyor (50) are conducted in a coordinated manner by the controller (40), and
wherein amounts of the first liquid ($F_1$) and the second liquid ($F_2$) to be applied on the substrate (S) depend on parameters including:
a gas pressure;
a resolution of a picture to be drawn on the substrate (S) with the liquids,
a diameter of a port of the nozzle (300b), and
a speed for conveying the substrate (S); and
wherein the application amounts of the first liquid ($F_1$) and the second liquid ($F_2$) on the substrate (S) can be adjusted by modifying the parameters.

5. The system (1) according to claim 1, wherein the first and second applicator (30a, 30b) are configured to be capable of reciprocal movement in a direction orthogonal to a conveying direction of the substrate (S), and
wherein the controller (40) is configured to be capable of simultaneously controlling the spraying operation and the reciprocal movement of the first and second applicator (30a, 30b) and the conveying operation of the conveyor (50) so that the first and second applicator (30a, 30b) and the conveyor (50) operate in a coordinated manner.

6. The system (1) according to claim 1, wherein the third applicator (30c) comprises at least one third valve (310c) that corresponds to the nozzle (300c) and is operable to be opened/closed so as to permit or block the flow of the third liquid (F3) to the nozzle (300c), and
wherein the controller (40) is configured to be capable of individually controlling an opening/closing operation of the first to third valves (310a, 310b, 310c).

7. The system (1) according to claim 1, wherein the pressured gas is pressured air.

8. The system (1) according to claim 1, wherein the substrate (S) is a sheet-like substrate of a cosmetic article.

9. A method for applying at least two kinds of liquid onto respective targeted areas of a substrate (S), using the system (1) according to claim 1, said method comprising:
providing a first liquid ($F_1$) from the first storage unit (10a), wherein the first fluid ($F_1$) is a first fluid formula;
providing a second liquid ($F_2$) from the second storage unit (10b), wherein the second fluid ($F_2$) is a second fluid formula;
providing a third fluid ($F_3$), wherein the third fluid ($F_3$) is a binder for separating the first liquid ($F_1$) and the second liquid ($F_3$) from each other from the third storage unit (10c);
applying the first liquid ($F_1$) to a targeted area for the first liquid ($F_1$) on the substrate (S) by an action of the pressured gas, using the first applicator (30a) while conveying the substrate (S) by a conveyor (50) along a direction parallel to a surface of the substrate (S), wherein the conveyer (50) is configured such that the substrate (S) is set on the conveyer (50);
applying the second liquid ($F_2$) to a targeted area for the second liquid ($F_2$) on the substrate (S) by the action of the pressured gas, using the second applicator (30b) while conveying the substrate (S) by the conveyor (50) along the direction parallel to the surface of the substrate (S);
applying the third liquid ($F_3$) to a boundary area between the targeted area for the first liquid ($F_1$) and the targeted area for the second liquid ($F_2$) on the substrate (S) by the action of the pressured gas, using the third applicator (30c) while conveying the substrate (S) by the conveyor (50) along the direction parallel to the surface of the substrate (S),
wherein the application of the first liquid ($F_1$), the application of the second liquid ($F_2$), and the application of the third liquid ($F_3$) and the conveying operation of the conveyor (50) are conducted in a coordinated manner by the controller (40), and
wherein amounts of the first liquid ($F_1$) and the second liquid ($F_2$) to be applied on the substrate (S) depend on parameters including:
a gas pressure;
a resolution of a picture to be drawn on the substrate (S) with the liquids,
a diameter of a port of the nozzle (300b), and a speed for conveying the substrate (S); and wherein the application amounts of the first liquid ($F_1$) and the second liquid ($F_2$) on the substrate (S) can be adjusted by modifying the parameters.

10. A product (M) produced by applying at least two kinds of liquid onto respective targeted areas of a substrate (S), using the system (1) according to claim 1.

11. The product (M) according to claim 10, wherein the application level per unit area of the liquids is at least 300 grams/m$^2$.

12. The product (M) according to claim 10, wherein the product (M) is a facial mask.

13. A method for applying at least two kinds of liquid onto respective targeted areas of a substrate (S), said method comprising:

providing a first liquid ($F_1$) a second liquid ($F_2$), and a third liquid ($F_3$) wherein the first liquid ($F_1$) is a first fluid formula, the second liquid ($F_2$) is a second liquid formula, and the third liquid ($F_3$) is a binder for separating the first liquid ($F_1$) and the second liquid ($F_2$) from each other;

applying the first liquid ($F_1$) to a targeted area for the first liquid ($F_1$) on the substrate (S) by an action of a pressured gas while conveying the substrate (S) by a conveyor (50) along a direction parallel to a surface of the substrate (S), wherein the conveyer (50) is configured such that the substrate (S) is set on the conveyer (50);

applying the second liquid ($F_2$) to a targeted area for the second liquid ($F_2$) on the substrate (S) by the action of the pressured gas while conveying the substrate (S) by the conveyor (50) along the direction parallel to the surface of the substrate (S), applying the third liquid ($F_3$) to a boundary area between the targeted area for the first liquid ($F_1$) and the targeted area for the second liquid ($F_2$) on the substrate (S) by the action of the pressured gas while conveying the substrate (S) by the conveyor (50) along the direction parallel to the surface of the substrate (S), wherein the application of the first liquid ($F_1$) and the application of the second liquid ($F_2$) and the conveying operation of the conveyor (50) are conducted in a coordinated manner, and wherein amounts of the first liquid ($F_1$) and the second liquid ($F_2$) to be applied on the substrate (S) depend on parameters including:

a gas pressure;

a resolution of a picture to be drawn on the substrate (S) with the liquids, a diameter of a port of the nozzle (300*b*), and a speed for conveying the substrate (S); and wherein the application amounts of the first liquid ($F_1$) and the second liquid ($F_2$) on the substrate (S) can be adjusted by modifying the parameters.

14. A product (M) produced by applying at least two kinds of liquid onto respective targeted areas of a substrate (S), using the method according to claim 11.

15. The product (M) according to claim 14, wherein the application level per unit area of the liquids is at least 300 grams/m$^2$.

16. The product (M) according to claim 14, wherein the product (M) is a facial mask.

\* \* \* \* \*

UNITED STATES PATENT AND TRADEMARK OFFICE
CERTIFICATE OF CORRECTION

PATENT NO. : 11,497,293 B2
APPLICATION NO. : 16/489621
DATED : November 15, 2022
INVENTOR(S) : G. Agarwal et al.

It is certified that error appears in the above-identified patent and that said Letters Patent is hereby corrected as shown below:

In the Claims

| Column | Line | |
|---|---|---|
| 10 | 42 | In Claim 1, change "$F_r$" to -- $F_1$ --. |
| 10 | 62 | In Claim 1, change "on" to -- one --. |
| 11 | 47 | In Claim 1, change "operayion" to -- operation --. |
| 12 | 25 | In Claim 2, change "on" to -- one --. |
| 13 | 10 | In Claim 2, change "operayion" to -- operation --. |
| 13 | 30 | In Claim 4, change "$F_3$" to -- $F_2$ --. |
| 14 | 34 | In Claim 9, change "$F_3$" to -- $F_2$ --. |

Signed and Sealed this
Eighth Day of August, 2023

Katherine Kelly Vidal
*Director of the United States Patent and Trademark Office*